(12) United States Patent
Li et al.

(10) Patent No.: US 9,820,855 B2
(45) Date of Patent: *Nov. 21, 2017

(54) PROSTHESIS AND METHOD FOR USING PROSTHESIS TO FACILITATE DEEP KNEE FLEXION

(71) Applicant: The General Hospital Corporation, Boston, MA (US)

(72) Inventors: Guoan Li, Milton, MA (US); Kartik Mangudi Varadarajan, Belmont, MA (US); Harry E. Rubash, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,694

(22) Filed: Jul. 2, 2015

(65) Prior Publication Data
US 2015/0297352 A1 Oct. 22, 2015

Related U.S. Application Data

(63) Continuation of application No. 13/886,512, filed on May 3, 2013, now Pat. No. 9,084,679.

(60) Provisional application No. 61/642,073, filed on May 3, 2012.

(51) Int. Cl.
*A61F 2/38* (2006.01)
*A61F 2/46* (2006.01)
*A61F 2/30* (2006.01)

(52) U.S. Cl.
CPC ............ *A61F 2/3859* (2013.01); *A61F 2/461* (2013.01); *A61F 2002/30326* (2013.01); *A61F 2002/30327* (2013.01); *A61F 2002/30934* (2013.01)

(58) Field of Classification Search
CPC ..................... A61F 2/3859; A61F 2002/30934
USPC ................................ 623/20.14, 20.31, 20.35
See application file for complete search history.

(56) References Cited

U.S. PATENT DOCUMENTS 5,824,105 A 10/1998 Ries et al.
6,770,099 B2 8/2004 Andriacchi et al.

OTHER PUBLICATIONS

Clary, et al., Management of MCL Tension in Deep Flexion: Influence of Implant Shape, Poster No. 1990, ORS 2012 Annual Meeting, 1 page.
Dennis, et al., Factors Affecting Flexion After Total Knee Arthroplasty, Clinical Orthopaedics & Related Research, 2007, 464:53-60.
Gandhi, et al., High-Flexion Implants in Primary Total Knee Arthroplasty: A Meta-Analysis, The Knee, 2009, 16(1):14-17.

(Continued)

*Primary Examiner* — David H Willse
*Assistant Examiner* — Javier Blanco
(74) *Attorney, Agent, or Firm* — Quarles & Brady LLP

(57) ABSTRACT

The present invention provides a femoral prosthesis for a femur which can enable or allow deep knee flexion without creating excessive tension in the ligamentous structure of the knee. The femoral prosthesis includes an internal non-articulating surface, an external articulating surface, a medial condyle and a lateral condyle. The height of the medial condyle is less than the height of the lateral condyle. A proximal-posterior tip of the medial condyle is rounded and is shifted inwards relative to the native level of the proximal-posterior region of the femur bone to facilitate knee flexion. A method of mounting a femoral prosthesis on a femur is also described.

8 Claims, 13 Drawing Sheets

(56) References Cited

OTHER PUBLICATIONS

Jeffcote, et al., The Variation in Medial and Lateral Collateral Ligament Strain and Tibiofemoral Forces Following Changes in the Flexion and Extension Gaps in Total Knee Replacement, J Bone Joint Surg (Br), 2007, 89-B:1528-1533.

Kurtz, et al., Projections of Primary and Revision Hip and Knee Arthroplasty in the United States from 2005 to 2030, J Bone Joint Surg Am, 2007, 89(4):780-785.

Kurtz, et al., International Survey of Primary and Revision Total Knee Replacement, Paper No. 214, Proceedings of the 56th Annual Meeting of the Orthopaedic Research Society, New Orleans, LA, Mar. 2010, 1 page.

Kuster, et al., Assessment of Isometricity Before and After Total Knee Arthroplasty: A Cadaver Study, The Knee, 2009, 16(5):352-357.

Nicholls, et al., Tibiofemoral Force Following Total Knee Arthroplasty: Comparison of Four Prosthesis Designs In Vitro, Journal of Orthopaedic Research, 2007, 25(11):1506-1512.

Noble, et al., Does Total Knee Replacement Restore Normal Knee Function?, Clinical Orthopaedics & Related Research, 2005, 431:157-165.

Nutton, et al., A Prospective Randomised Double-Blind Study of Functional Outcome and Range of Flexion Following Total Knee Replacement with the NexGen Standard and High Flexion Components, J Bone Joint Surg (Br), 2008, 90-B:37-42.

Sultan, et al., Optimizing Flexion After Total Knee Arthroplasty: Advances in Prosthetic Design, Clinical Orthopaedics & Related Reseach, 2003, 416:167-173.

Varadarajan, et al., Tibiofemoral Joint Space Measured During Weight-Bearing Knee Flexion Increases Following TKA, Poster No. 2062, Proceedings of the 56th Annual Meeting of the Orthopaedic Research Society, New Orleans, LA, Mar. 2010, 1 page.

PROSTHESIS AND METHOD FOR USING PROSTHESIS TO FACILITATE DEEP KNEE FLEXION

CROSS-REFERENCES TO RELATED APPLICATIONS

This application is a continuation of U.S. Ser. No. 13/886,512 filed May 3, 2013, now U.S. Pat. No. 9,084,679, which claims the benefit of, and incorporates herein by reference, U.S. Provisional Patent Application Ser. No. 61/642,073, filed on May 3, 2012.

STATEMENT REGARDING FEDERALLY SPONSORED RESEARCH

Not Applicable.

BACKGROUND OF THE INVENTION

The present invention relates to systems and methods for prosthetics and, more particularly, to systems and method for femoral prosthesis for knee replacement implants and methods of using femoral prosthesis for knee replacement.

Knee replacement procedures, such as total knee arthroplasty ("TKA") are a highly successful surgical treatment option for severe knee joint diseases, such as osteoarthritis and rheumatoid arthritis. However, several biomechanical and clinical studies have shown that current TKA prostheses do not fully restore the normal function of the knee. Typically, the active range of knee flexion following TKA is less than 115 degrees, whereas the healthy knee is capable of knee flexion up to 160 degrees (Sultan P G et al., Optimizing Flexion After Total Knee Arthroplasty: Advances in Prosthetic Design, Clin Orthop Relat Res. 2003:167-173; Dennis D A et al., Factors Affecting Flexion After Total Knee Arthroplasty, Clin Orthop Relat Res. 2007; 464:53-60). Even when compared to age-matched control population, TKA patients have been shown to have reduced knee flexion range. For example, Nutton et al. showed that the average active flexion range for TKA patients was 110 degrees (average age 71 years), whereas the age matched control population (average age 69 years) had average active knee flexion range of 134 degrees (Nutton R W et al., A Prospective Randomised Double-blind Study of Functional Outcome and Range of Flexion Following Total Knee Replacement with the NexGen Standard and High Flexion Components, J Bone Joint Surg Br. 2008; 90(1):37-42). Similarly, Noble et al. found that TKA patients had more functional impairment compared to normal subjects of similar age, particularly with regards to deep knee flexion activities involving kneeling and squatting (Noble P C, Gordon M J et al., Does Total Knee Replacement Restore Normal Knee Function, Clin Orthop Relat Res. 2005; 431:157-165).

These types of activities are particularly important for occupations such as roof tiling, leisure activities such gardening, and patients from certain ethnic and cultural backgrounds (e.g. Japan, India, China, and other Asian and Mideastern countries) (Sultan P G et al., Optimizing Flexion After Total knee Arthroplasty: Advances in Prosthetic Design, Clin Orthop Relat Res. 2003:167-173; Dennis D A et al., Factors Affecting Flexion After Total Knee Arthroplasty, Clin Orthop Relat Res. 2007; 464:53-60). Increased range of knee flexion is also important for meeting the higher demands of younger patients who are increasingly receiving these prostheses. In recognition of these needs, several major orthopaedic companies have put forth so-called high-flexion TKA prostheses (e.g. Sigma CR150 High Flex from Depuy Inc, and NexGen CR-Flex from Zimmer Inc). However, recent studies have shown that these High-Flexion TKA prostheses offer no advantage over standard prostheses with regards to increasing the range of knee flexion (Gandhi R et al., High-flexion Implants in Primary Total Knee Arthroplasty: a Meta-analysis, Knee, 2009; 16(1):14-7).

One of the causes for restricted knee flexion range with current TKA protheses is that they create excessive tension in the ligamentous structure of the knee in deep flexion. Deep flexion of the knee is generally described as flexion greater than about 115 degrees flexion. This may result from overstuffing of the flexion joint space by the prosthetic components (Varadarajan K M et al., Tibiofemoral Joint Space Measured During Weight-Bearing Knee Flexion Increases Following TKA, Proceedings of 56th Annual Meeting Orthop Res Soc, New Orleans, La., March 2010). In a series of inter-related studies Jeffcote et al., Nicholls et al. and Kuster et al. used a combination of miniature force plates and spring loaded rods to understand the pattern of soft tissue tension in the native knee and in the knee after implantation of contemporary (prior art) TKA prosthesis (Jeffcote B et al., The Variation in Medial and Lateral Collateral Ligament Strain and Tibiofemoral Forces Following Changes in the Flexion and Extension Gaps in Total Knee Replacement, A Laboratory Experiment Using Cadaver Knees, J Bone Joint Surg Br. 2007 November; 89(11):1528-33; Nicholls R L et al., Tibiofemoral Force Following Total Knee Arthroplasty: Comparison of Four Prosthesis Designs in Vitro. J Orthop Res. 2007 November; 25(11):1506-12; Kuster M S et al, Assessment of Isometricity Before and After Total Knee Arthroplasty: a Cadaver Study. Knee. 2009 October; 16(5):352-7). In these studies the soft tissue tension in the native knees was found to be relatively low and uniform in the 15-90 degrees flexion range, such as further illustrated in the graphs of FIGS. 1A and 1B. The native knees were also slightly tighter in full extension (0 degrees flexion), and gradually tightened from 90 degrees to 150 degrees flexion. Here, tightness of the joint implies increased soft tissue tension. Following implantation of contemporary TKA prosthesis, the knees showed a similar pattern of soft tissue tension as the native knees in the 0-90 degrees flexion range, such as indicated in FIGS. 1A and 1B. However, beyond 90 degrees flexion the TKA knees showed a rapid increase in soft tissue tension. This was seen for various contemporary TKA designs particularly those involving the retention of the posterior cruciate ligament (Nicholls R L et al., Tibiofemoral Force Following Total Knee Arthroplasty: Comparison of Four Prosthesis Designs in Vitro, J Orthop Res. 2007 November; 25(11): 1506-12). This excessive tightening of the soft tissues of the knee in deep flexion could contribute to the restricted range of knee flexion following implantation of contemporary TKA prosthesis.

The above studies were done on cadaver knees under non-weightbearing conditions. However, these findings are also supported by a more recent study wherein the tibiofemoral joint space in knees of TKA patients was measured during a weight-bearing activity, and compared to tibiofemoral joint space in healthy knees of normal subjects (Varadarajan K M, Yue B., Moynihan A L, Seon J K, Freiberg A A, Rubash H E, Li G., Tibiofemoral Joint Space Measured During Weight-Bearing Knee Flexion Increases Following TKA. Proceedings of 56th Annual Meeting Orthop Res. Soc., New Orleans, La., March 2010). This study found that the TKA knees showed increased tibiofemoral joint space compared to healthy knees for flexion above 90 degrees, such as further illustrated in the graph of FIG. 2. Herein, the tibiofermoral joint space was defined as the distance between a point on the femur bone and a point on the tibia bone measured in the proxima-distal direction. Most TKA patients in this study could not bend their knees beyond 110 degrees flexion. The increased tibiofemoral joint space in flexion may be lead to increased soft tissue tension, which may contribute to restricted range of knee flexion with prior art TKA prosthesis.

Therefore, it would be desirable to have a system and method that can provide deep knee flexion without creating excessive tension in the ligamentous structure of the knee, and thereby to restore native anatomy and function of the knee.

SUMMARY OF THE INVENTION

The foregoing needs are met by providing a femoral prosthesis, which can facilitate or allow deep knee flexion without creating excessive tension in the ligamentous structure of the knee. The design of this prosthesis can prevent over tensioning of the ligaments in deep flexion, thereby facilitating increased range of motion.

In one aspect, the present disclosure provides a prosthesis is disclosed for a femur configured to control over-stretching of soft tissue in deep knee flexion. The prosthesis includes an internal non-articulating surface and an external articulating surface. The external articulating surface includes a distal articulating surface, a medial posterior surface having a first medial end and a second medial end, and a lateral posterior surface having a first lateral end and a second lateral end. The first medial end and the first lateral end are connected to the distal articulating surface. The prosthesis also includes a medial condyle extending from the first medial end to the second medial end and formed between the medial posterior surface and the internal non-articulating surface and a lateral condyle extending from the first lateral end to the second lateral end and formed between the lateral posterior surface and the internal non-articulating surface. A first height of the medial condyle is measured from a line tangent to the distal articulating surface to the second medial end and is less than a second height of the lateral condyle measured from the line tangent to the distal articulating surface to the second lateral end.

In another aspect, the present disclosure provides a method is provided for mounting a femoral prosthesis on a distal end of a femur associated with a knee and a leg to control over-stretching soft tissue in deep knee flexion. The method includes providing a femoral prosthesis with a distal articulating surface and a lateral posterior surface, removing a portion of a proximal-posterior bone of the femur, and mounting the femoral prosthesis on the femur. The femoral prosthesis is mounted to the femur such that the distal articulating surface is tangent to a cartilage surface on a lateral side of the knee, the distal articulating surface is perpendicular to a mechanical axis of the femur, and the lateral posterior surface is tangent to a posterior cartilage surface on the lateral side of the knee.

These and other features, aspects, and advantages of the present invention will become better understood upon consideration of the following detailed description, drawings and appended claims.

BRIEF DESCRIPTION OF THE DRAWINGS

In the following drawings, like reference numerals will be used to refer to like parts from Figure to Figure.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. The definitions of a terms used to describe the present invention are provided below.

The term "native" is used herein to imply natural or naturally occurring in the body. Examples of native structures include musculoskeletal structures such as the femoral bone (or femur), tibial bone (or tibia), tendon, muscle, ligament, and the like.

The terms "articulate" and "articulating", are used herein to indicate the possibility of relative motion at a surface. For prosthetic components such relative motion is intended or part of the design intent. For example, "component A articulates with component B", indicates that relative motion can occur between component A and component B at the mating surface/s or interface/s.

The term "articular surface" as used herein refers to a portion of a native musculoskeletal structure or a prosthetic component where relative motion (or articulation) can occur in relation to another native structure or prosthetic component.

Figure 4A:
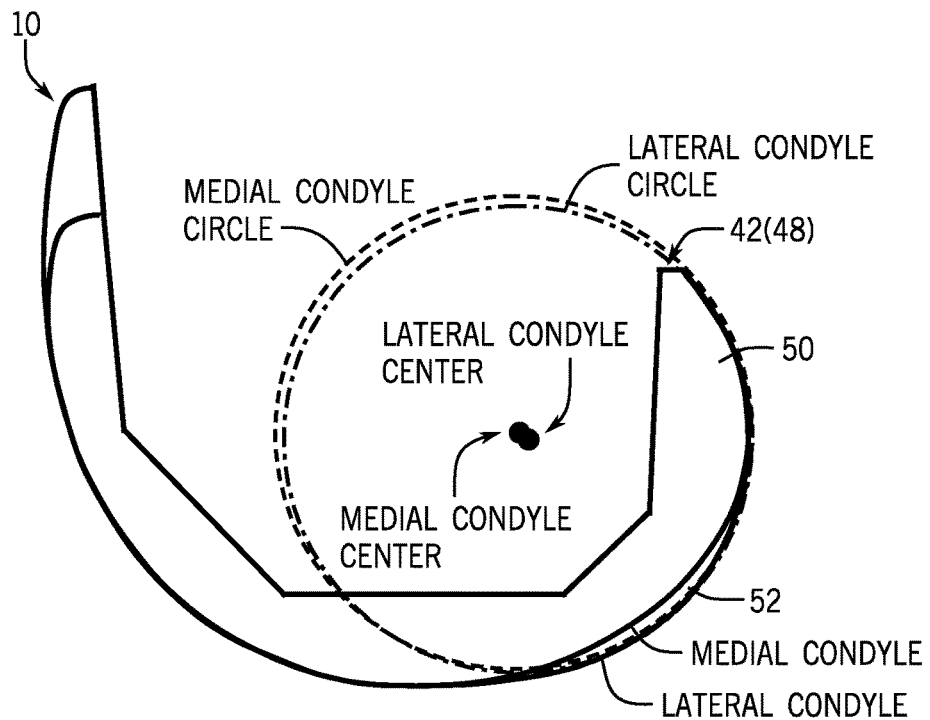
FIG. 4A provides a side view of a prior art femoral prosthesis, displaying the profiles of the medial and lateral condyles of the femoral prosthesis. Circles fit to the distal-posterior profile of the medial/lateral condyle in the side view are defined as medial/lateral condyle circles. Centers of these circles are defined as medial/lateral condyle centers.

The term "condyle circle" as used herein is a circle that best fits or approximates the distal-posterior profile of a femoral condyle, such as a medial or lateral femoral condyle, as seen in a side view. The center of a condyle circle as seen in a side view is defined as the "condyle center" (FIG. 4A).

The term "inwards" as used herein means toward the inside or toward the interior, such as toward or closer to a center. For example, a portion of an outer surface of a medial or lateral condyle of a femoral prosthesis may be shaped, designed or contoured to move or shift the surface inwards toward the condyle center.

The term "outwards" as used herein means away from the inside or toward the exterior, such as away from a center. For example, a portion of an outer surface of a medial or lateral condyle of a femoral prosthesis may be shaped, designed or contoured to move or shift the surface outwards, away from the condyle center and towards the exterior.

Figure 6A:
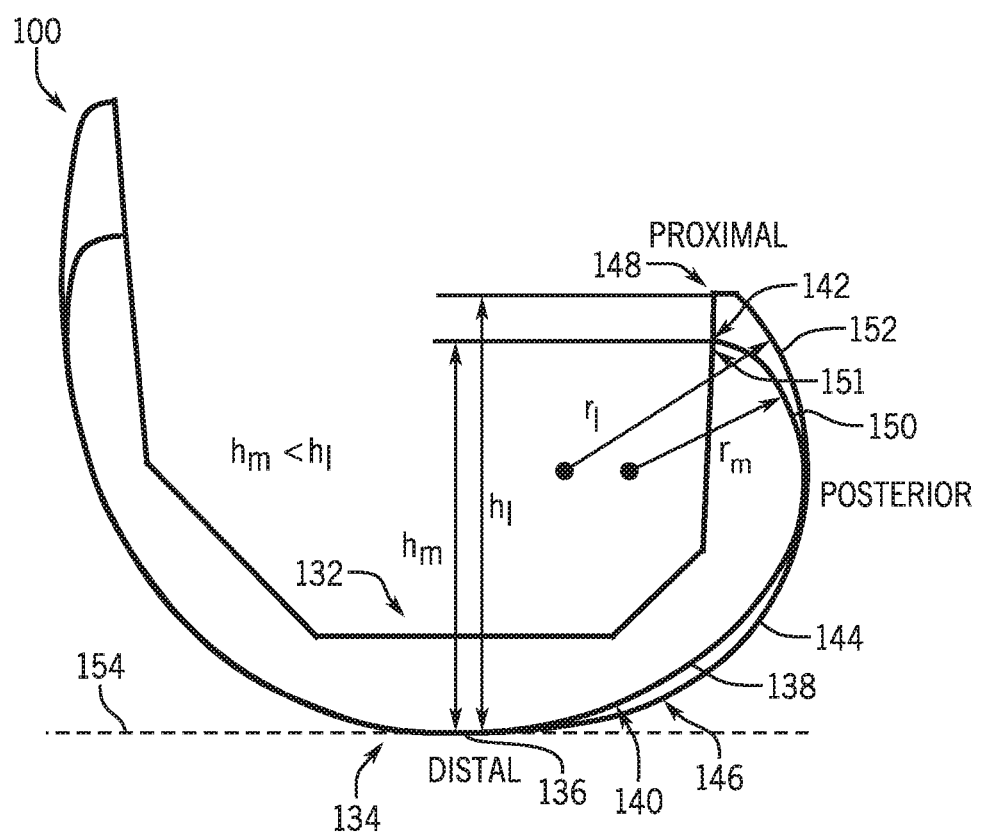
FIG. 6A shows a side view of one embodiment of the femoral prosthesis of the present invention, displaying the profiles of the medial and lateral condyles. Herein the height of the medial femoral condyle of the novel femoral prosthesis is less than the height of the lateral femoral condyle (hm<hl), and the proximal-posterior articulating surface of the medial femoral condyle is shifted inwards relative to the proximal-posterior portion of the lateral femoral condyle.
Figure 7A:
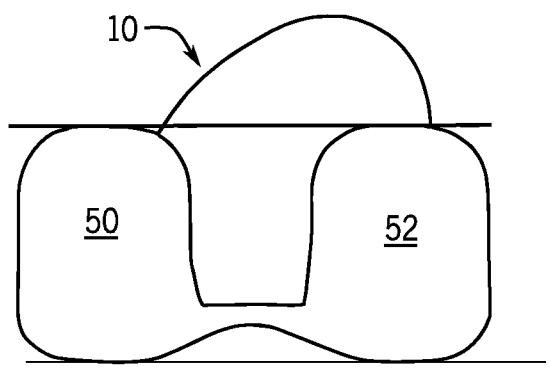
FIG. 7A shows a posterior view of a prior art TKA femoral prosthesis in which the medial and lateral condyle heights are equal.
Figure 7B:
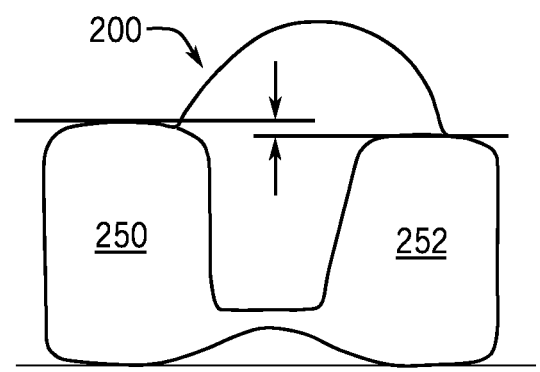
FIG. 7B provides a posterior view of another prior art TKA femoral prosthesis in which the medial condyle height is greater than the lateral condyle height.
Figure 7C:
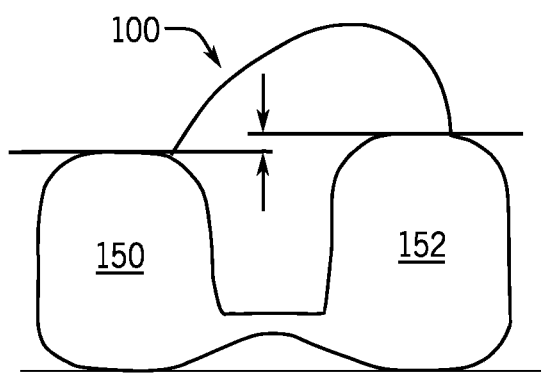
FIG. 7C provides a posterior view of a femoral prosthesis in accordance with the present disclosure in which the medial condyle height is lower than the lateral condyle height.

The term "condyle height" as defined and used herein is the distance between a line or plane tangent to the distal articulating surface of the condyle and another line or plane tangent to a proximal end of the condyle, for example as may be additionally understood from FIGS. 6A and 7C.

Figure 1A:
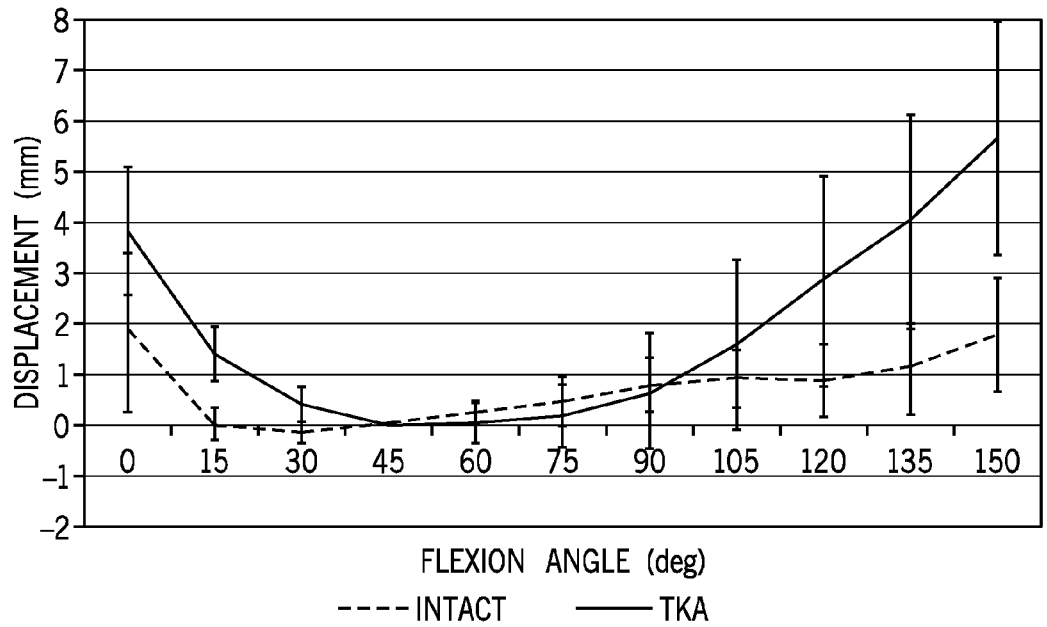
FIG. 1A provides a plot of displacement of a floating rod in the intact and TKA knees as a function of knee flexion angle. This is used to characterize soft tissue tension pattern, where higher displacement values correspond to greater soft tissue tension, in accordance with prior art.
Figure 1B:
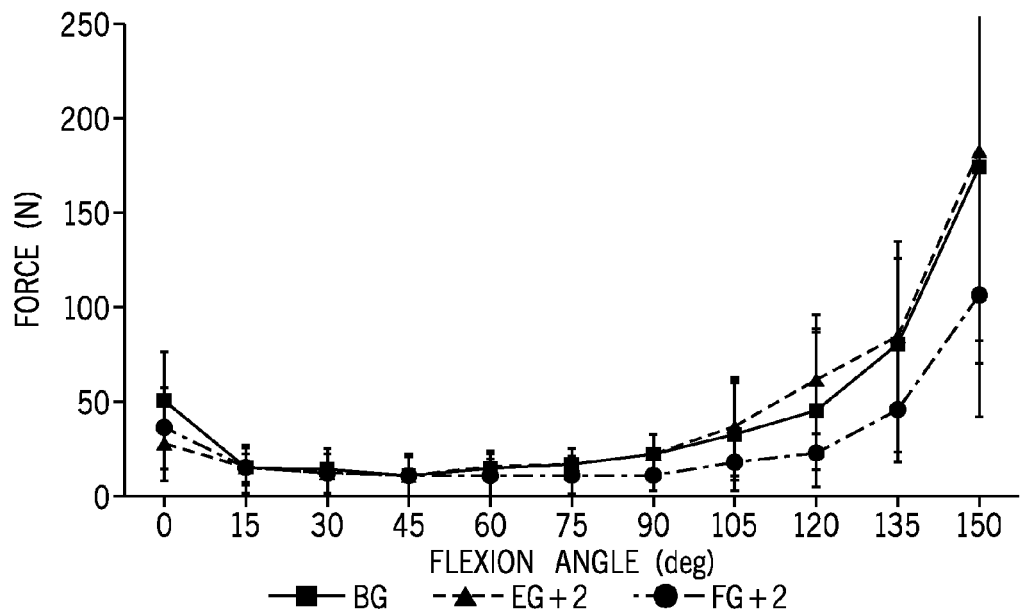
FIG. 1B shows a plot of tibiofemoral joint compression force as a function of flexion angle in a knee with prior art TKA prosthesis following standard joint balancing procedure (BG=balanced gap), and experimental modifications involving increasing the extension gap (EG) and flexion gap (FG) by 2 mm. This is used to characterize soft tissue tension pattern, where higher force values correspond to greater soft tissue tension and generally indicate greater tightness, in accordance with prior art.
Figure 2:
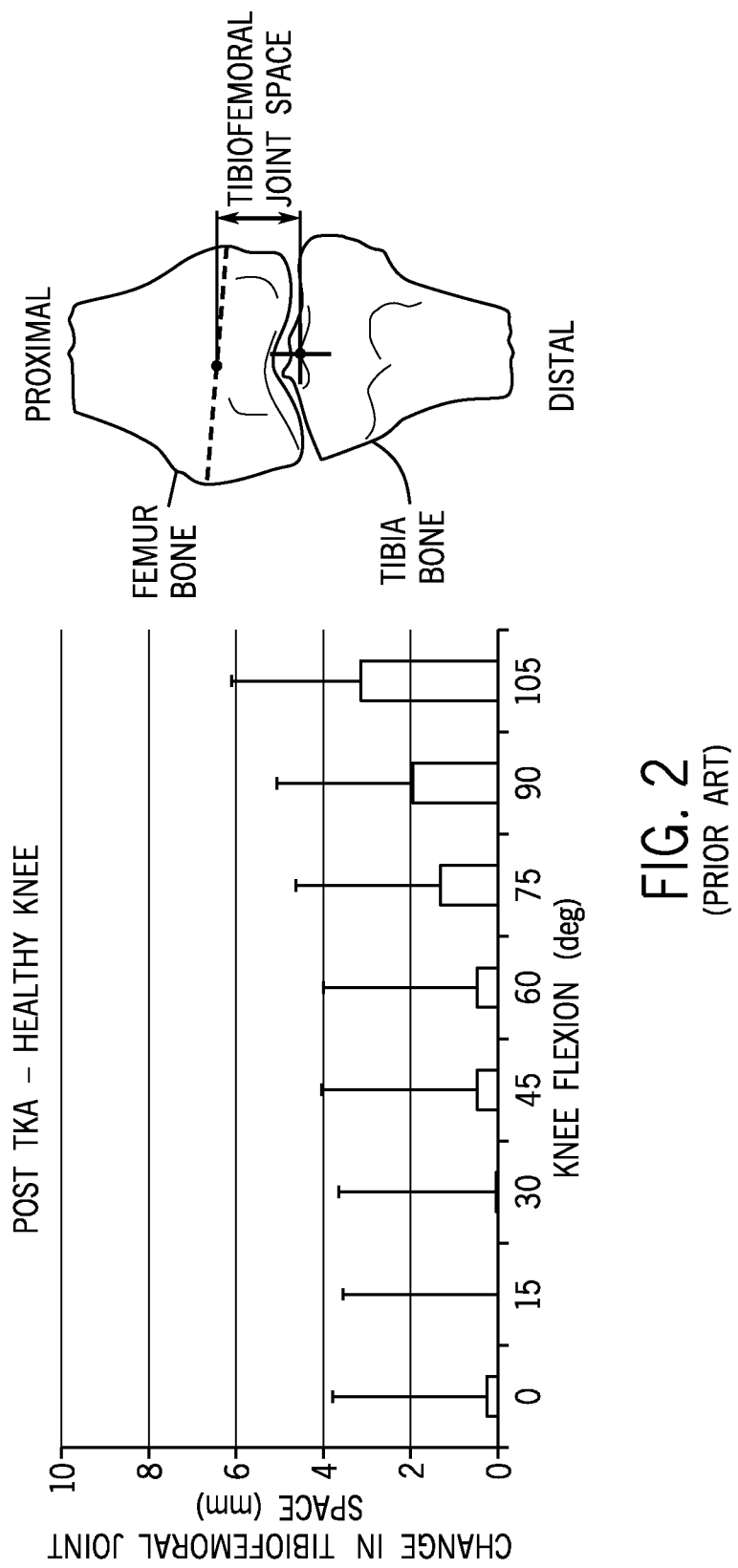
FIG. 2 provides a plot of tibiofemoral joint space measured in knees of patients with prior art TKA prosthesis post-surgery minus the corresponding joint space in the knees of healthy subjects, as a function of knee flexion angle, where above 75 degrees flexion, the tibiofemoral joint space in the TKA knees increased rapidly compared to the corresponding values in healthy knees, in accordance with prior art.
Figure 3B:
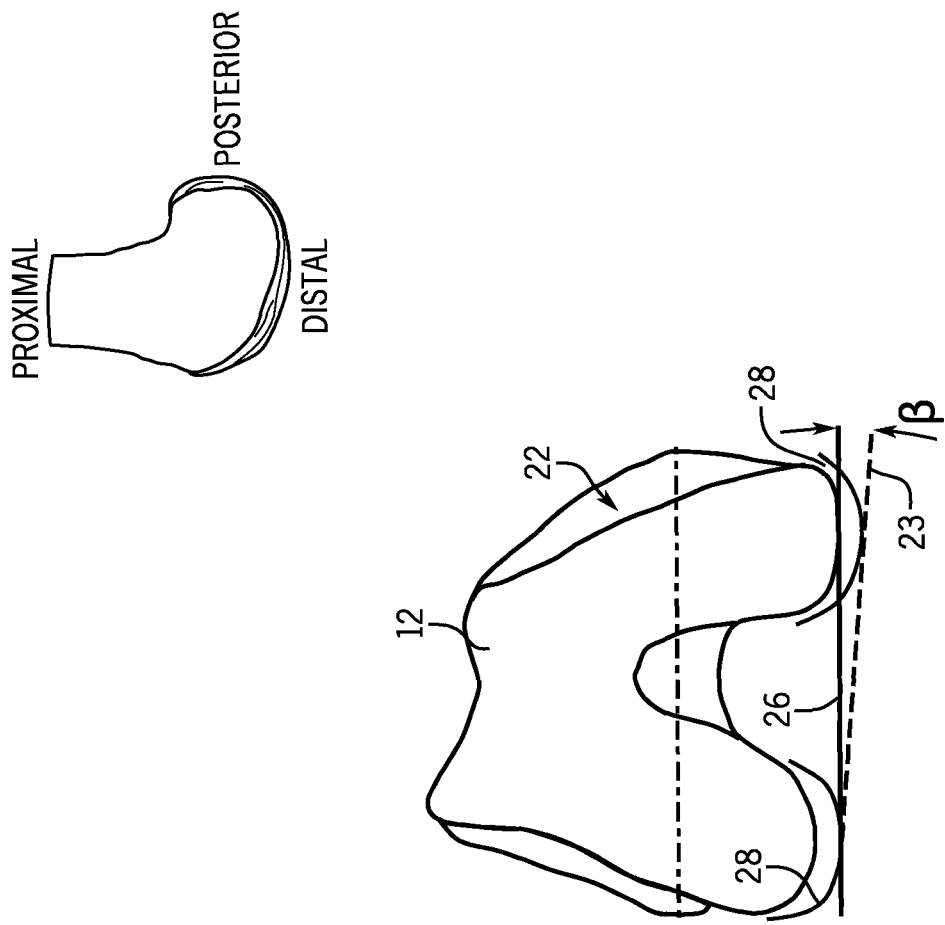
FIG. 3B provides a top elevational view illustrating the procedure of FIG. 3A, in which the posterior surface of the femoral prosthesis is aligned tangent to the lateral cartilage, with approximately 3 degrees of rotation ($\alpha$) relative to a line tangent to the medial and lateral femoral cartilage surface.
Figure 3A:
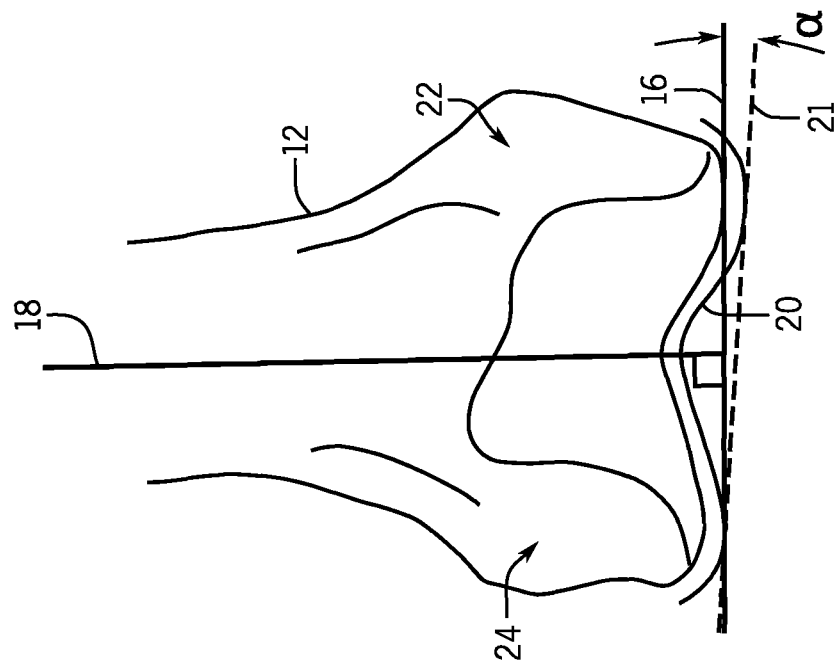
FIG. 3A provides a front elevational view illustrating a native femur, indicating the alignment/positioning of a femoral prosthesis on the native femur following standard surgical procedure which aligns the femoral prosthesis perpendicular to the femoral mechanical axis and tangent to the lateral femoral cartilage, in accordance with prior art.

Referring to FIGS. 3A and 3B, the orientation or positioning of a femoral prosthesis on a distal end of a femur bone following standard TKA surgical procedure is shown. A femoral prosthesis is generally mounted such that the distal surface 16 of the prosthesis will be approximately perpendicular to the mechanical axis 18 of the femur 12. In order to mount the femoral prothesis on the femur 12, the cartilaginous surface 20 of the side with relatively normal anatomy is typically used as reference. As the majority of the surgical cases (greater than about two-thirds) involve disease of the medial side 22 of the knee, the lateral side 24 of the knee is typically used as the reference.

Referring to FIG. 3A, a femoral prosthesis is mounted such that on the lateral side 24 of the knee, a distal surface 16 of the prosthesis is oriented on a line 21 tangent to the original cartilage surface 20 on the lateral side 24 of the knee. The distal surface 16 of the prosthesis is then oriented to be perpendicular to the mechanical axis 18 of the femur 12. This results in the distal surface 16 of the femoral prosthesis approximately matching the level of the native femoral bone 12 on the medial side 22. The angle α created by the rotation between the initial orientation of the distal surface 16 along line 21 to its final orientation to be perpendicular to the mechanical axis 18 of the femur 12 is approximately equal to three degrees, however, it can be appreciated that this angle α may vary. For example, α maybe in the range of 1 degree to 10 degrees, 3 degrees to 7 degrees, 4 degrees to 6 degrees, and the like.

Turning now to FIG. 3B, the orientation for the posterior surface 26 of a prosthesis is shown. The posterior surface 26 is positioned to match the posterior cartilage surface 28 on the lateral side 24 of the knee, as referenced by line 23. Similar to the rotation described above, the posterior surface 26 is rotated such that the posterior surface 26 approximately matches the level of the native femoral bone 12 on the medial side 22 of the knee. The angle β created by the rotation between the initial orientation of the posterior surface 26 along line 23 to its final orientation is approximately equal to three degrees, however, it can be appreciated that this angle β may vary. For example, β maybe in the range of 1 degree to 10 degrees, 3 degrees to 7 degrees, 4 degrees to 6 degrees, and the like.

The orientation of the distal and posterior surfaces 16, 26 of a femoral prosthesis as described achieves a symmetric joint space to enable equal tensioning of the medial and lateral collateral ligaments in the 0 degrees to 90 degrees flexion range in the distal 29 and posterior 31 regions of the femur 12. As such, components for a standard TKA femoral prosthesis 10 are designed to allow the distal surface 16 to be perpendicular to the mechanical axis 18 while achieving equal medial/lateral ligament tension from 0 to 90 degrees flexion. However, this does not account for ligamentous function beyond 90 degrees flexion. Therefore, when the above surgical procedure is employed with a standard prosthesis 10, prior art prostheses such as shown in figures FIGS. 4B and 5A, the medial posterior surface 38 of the prosthesis 10 does not match the femoral bone surface 13 at flexion angles greater than 90 degrees, such as further illustrated in FIGS. 4B, 4C, 5A and 5B. This provides that when the knee is in a state of flexion beyond 90 degrees, the traditional femoral prostheses do not match the level of the native femoral bone surface 13 in the proximal-posterior region 27 on the medial side. This can lead to excessive ligament tension in the knee, particularly in medial structures of the knee such as the medial collateral ligament, and structures that attach to the medial femoral condyle, such as the posterior cruciate ligament.

Figure 6B:
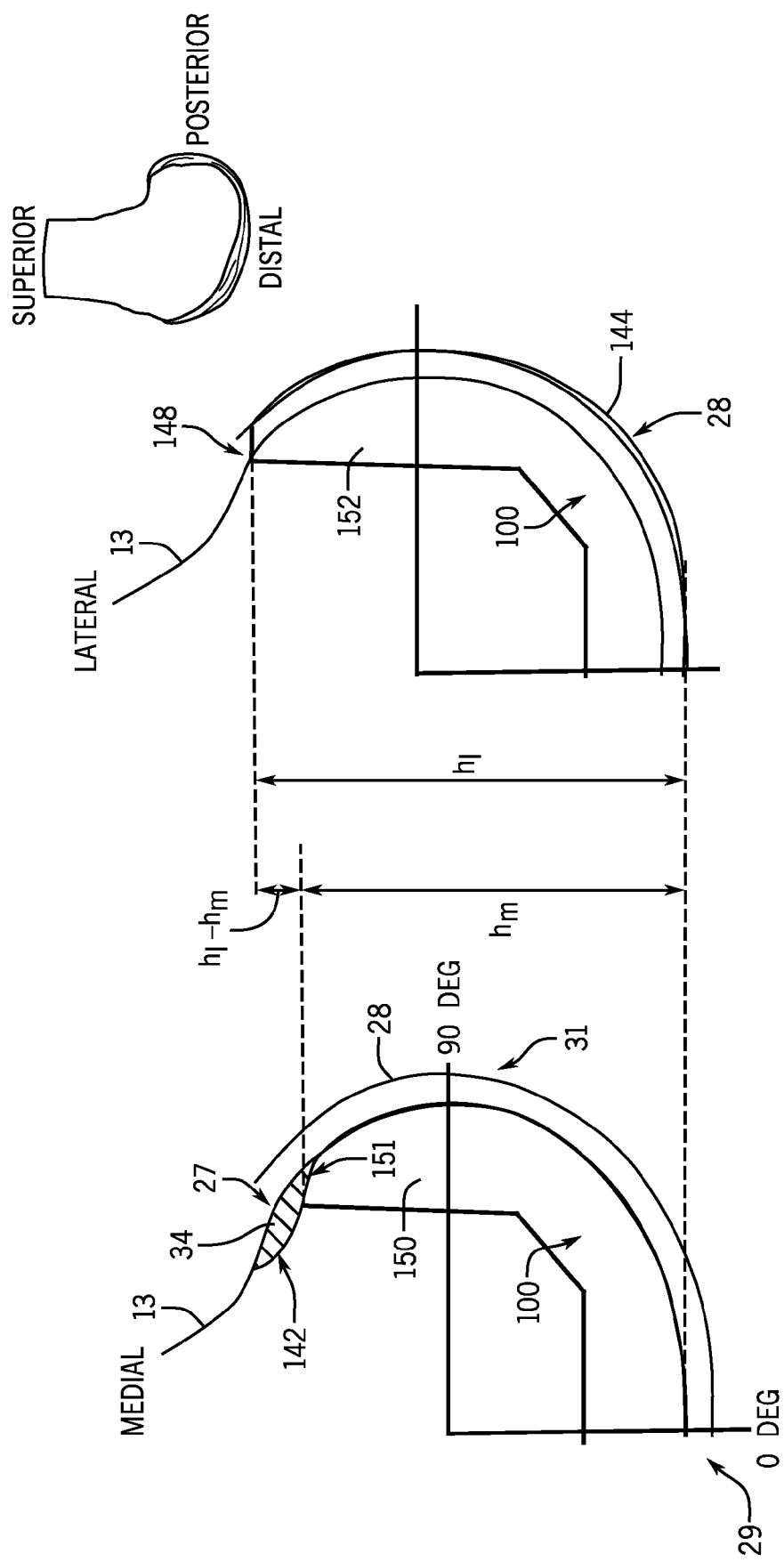
FIG. 6B shows sagittal sectional views of one embodiment of the femoral prosthesis of the present invention taken parallel to the femoral mechanical axis displaying both the medial and lateral femoral condyles in which on the medial side, the prosthesis matches the level of the femoral bone in the distal, posterior, and proximal-posterior regions, and the proximal most tip/end of the medial condyle is rounded and lowered below the level of the native femur bone i.e. shifted inwards relative to the native femur bone.

Turning now to FIGS. 6A and 6B, a femoral prosthesis design 100 in accordance with the present disclosure is shown. The prosthesis 100 includes an internal non-articulating surface 132. The internal non-articulating surface 132 is connected to the resected distal end of a femur 12 during surgery, as one of ordinary skill in the art of TKA is familiar, such as with bone cement. The femoral prosthesis design 100 also includes an external articulating surface 134 that engages and articulates with the tibial component (not shown) of the TKA prosthesis. The external articulating surface 134 includes a distal articulating surface 136 and a medial posterior surface 138 that has a first medial end 140 and a second medial end 142. The external articulating surface 134 also includes a lateral posterior surface 144 that has a first lateral end 146 and a second lateral end 148. The first medial end 140 and the first lateral end 146 are connected to the distal articulating surface 136. A medial condyle 150 extends from the first medial end 140 to the second medial end 142 and is formed between the medial posterior surface 138 and the internal non-articulating surface 132. The medial condyle 150 includes a proximal-posterior tip or end 151. A lateral condyle 152 extends from the first lateral end 146 to the second lateral end 148 and is formed between the lateral posterior surface 144 and the internal non-articulating surface 132.

The femoral prosthesis 100 is configured such that the height of the medial condyle 150 is less than the height of the lateral condyle 152, as best shown in FIG. 6(A). The heights of the condyles 150, 152 are measured from a line 154 that is tangent to the distal articulating surface 136 to the second medial end 142 and second lateral end 148, respectively. In one embodiment, the medial condyle height $h_m$ is about 35.5 mm, but can be in the range of 20 mm to 60 mm, 30 mm to 45 mm, 35 mm to 40 mm and the like. In one embodiment the lateral condyle height $h_l$ is about 38.5 mm, but can be in the range of 22 mm to 62 mm, 32 mm to 47 mm, 37 mm to 42 mm and the like. The difference in height between the medial condyle 150 and the lateral condyle 152 ($h_l-h_m$) can be in the range of about 0.5 mm to 6 mm, about 1 mm to 4 mm, about 2 mm to 3 mm and the like. In one embodiment for the femoral prosthesis 100, the difference in height is about three millimeters. This height difference between the medial and lateral condyles 150, 152 is also shown in FIG. 7C from a rear, or posterior, view of the femoral prosthesis design 100, as well as in FIG. 6A. This is in contrast to the traditional femoral prosthesis 10, as shown in FIGS. 7A and 7B, which have either equal medial and lateral condyle 50,52 heights ($h'_m=h'_l$) or the medial condyle height 50 is greater than that of the lateral condyle 52 ($h''_m>h''_l$, see U.S. Pat. No. 6,770,099 to Andriacchi et al.). In the embodiment, as illustrated in FIG. 6A, the outer articulating surface of the medial femoral condyle in the proximal-posterior is also shifted inwards relative to the proximal-posterior surface of the lateral femoral condyle. In some configurations this may be achieved by using a radius $r_m$ that is less than the radius $r_l$, of the lateral condyle 152. In other configurations of the design, the proximal-posterior portions of the medial and lateral femoral condyles may be composed of one or more radii. These radii (including $r_m$ and $r_l$) can have any value, such as in the range of 2 mm to 70 mm, 10 mm to 40 mm, 25 mm to 30 mm and the like. In one embodiment of the femoral prosthesis, $r_m$ is about 13.5 mm and $r_l$ is about 20 mm.

The femoral prosthesis design 100 described herein controls excessive ligament tension by having a medial proximal-posterior geometry that matches the femoral bone surface 13 even at flexion angles greater than 90 degrees, such as further illustrated in FIG. 6B. In addition to the medial femoral condyle 150 height being lowered relative to the lateral femoral condyle 152 as discussed above, the outer surface of the medial condyle 150 is shifted inwards from the posterior cartilage surface 28. As shown in FIG. 6B, this may result in the medial femoral condyle surface 150 being pushed inwards i.e. towards the anterior of the knee approximately 2.5 mm from the original posterior cartilage surface 28 to more closely match the bone surface 13 geometry in the posterior region 31. The proximal-posterior tip 151 of the medial condyle 150 may also be rounded to match the geometry of the bone surface 13. Because the medial femoral condyle 150 is lowered relative to the lateral femoral condyle 152, a portion of the proximal-posterior bone 34 may be removed during surgery to avoid impingement of the bone 34 with the tibial component (not shown) of the TKA prosthesis in very deep flexion (greater than about 135 degrees). As shown in FIG. 6B, this portion of the proximal-posterior bone 34 that may be removed may be from the medial 22 bone surface 13. Removing the proximal-posterior bone 34 and aligning the second medial end 142 of the medial condyle 150 to match the bone surface 13 results in the proximal-posterior tip 151 to be lower than the native bone surface 13 of the proximal-posterior region 27 of the femur 12.

Figure 8A:
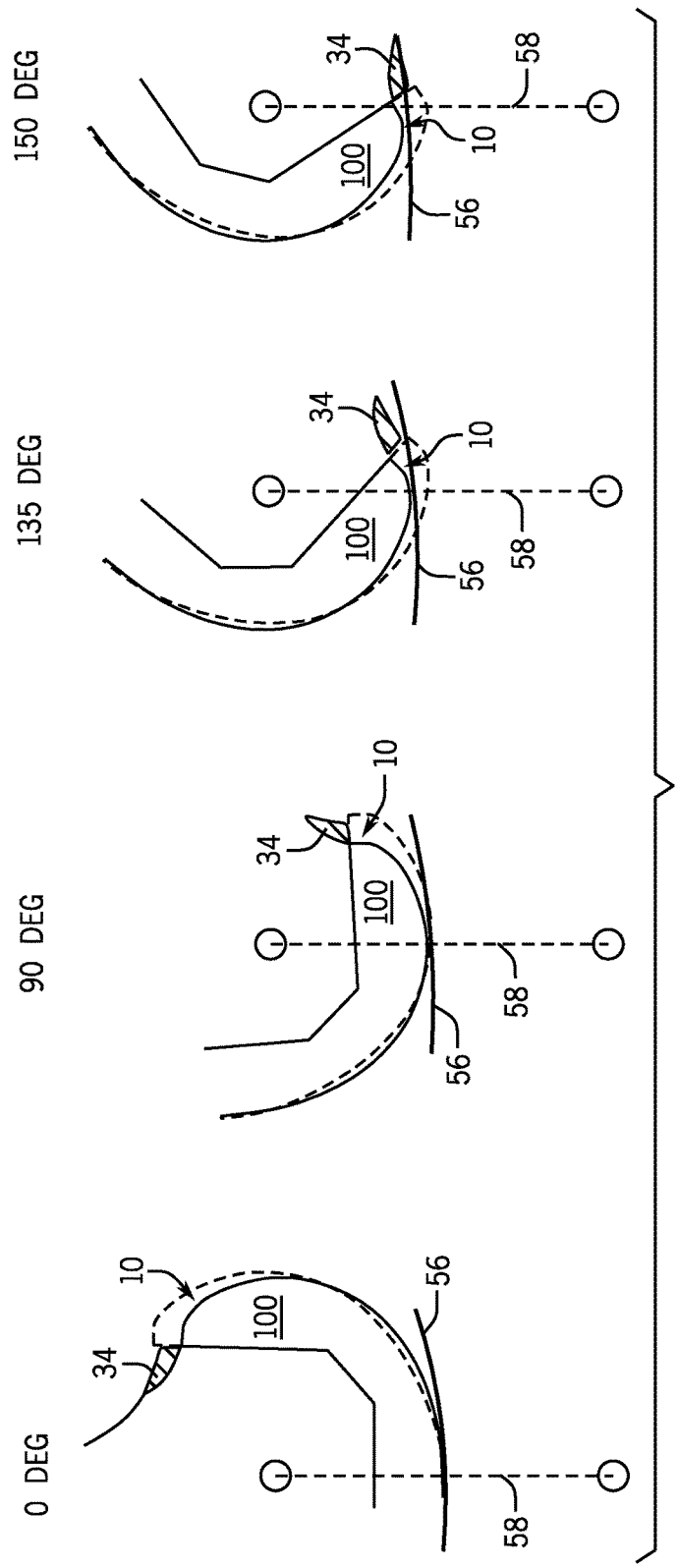
FIG. 8A shows medial side views of a femoral prosthesis in accordance with the present disclosure in varying degrees of flexion, in which the femoral prosthesis allows for uniform ligament tension throughout the full range of knee motion including deep flexion, with the profile of a standard femoral prosthesis of FIG. 4B being shown for comparative purposes.
Figure 8B:
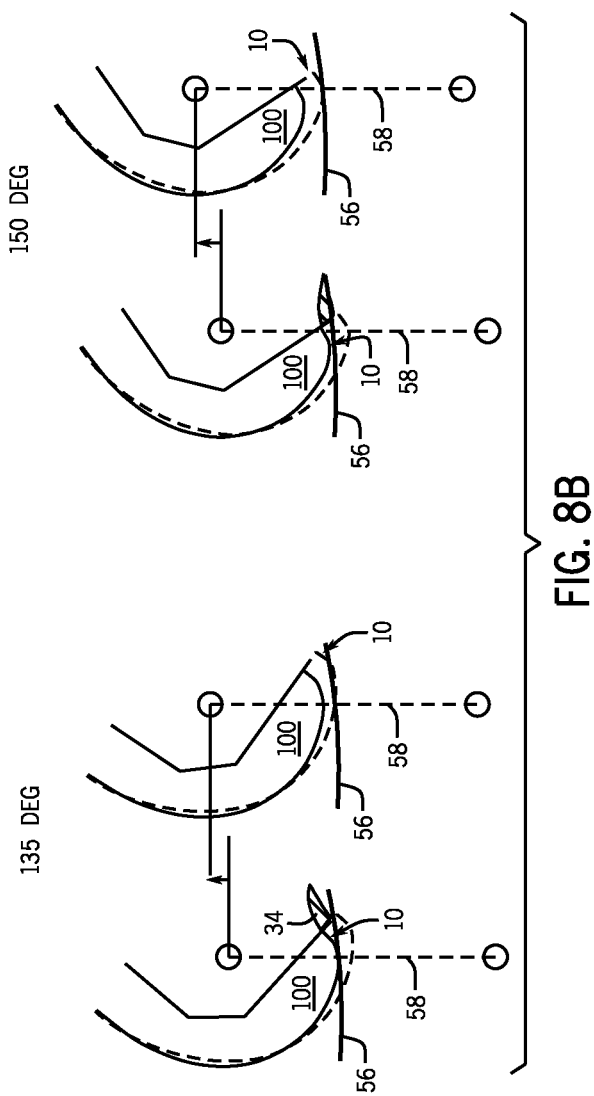
FIG. 8B provides side views displaying the difference between a standard femoral prosthesis of FIG. 4B, and a femoral prosthesis in accordance with the present invention in varying degrees of deep flexion, in which the standard femoral prosthesis results in over tensioning of the ligaments in deep flexion.

FIGS. 8A and 8B illustrate how the femoral prosthesis 100 avoids over stretching of the soft tissue in deep flexion, particularly overstretching of the medial soft-tissues. FIG. 8A follows flexion from 0 degree to 150 degrees for a knee that has a prosthesis 100, but also displays the profile of the traditional femoral prosthesis 10 for comparison. The tibial component 56 and medial collateral ligament 58 are also shown in FIGS. 8A and 8B. As the knee bends from 0 degrees through 90 degrees flexion, both the prosthesis 10 and femoral prostheses 100 allow the medial soft tissue to maintain uniform tension. As shown in FIG. 8A, the medial collateral ligament 58 in a knee with the prosthesis 100 design does not experience increased tension as the knee is flexed, even for flexion beyond 90 degrees. Also of note in FIG. 8A, the removal of the proximal-posterior bone 34 allows the femoral prosthesis 100 to avoid contact with the tibial component 56 of the prosthesis.

However, for a knee with a traditional femoral prosthesis 10, the situation changes for flexion of the knee beyond 90 degrees. FIG. 8B shows a comparison of a knee with a traditional femoral prosthesis 10 to a femoral prosthesis 100 as described herein for flexion angles of 135 degrees and 150 degrees. As shown in FIG. 8B, for the traditional TKA femoral prosthesis 10 to flex beyond 90 degrees and maintain uniform ligamentous tension, the traditional femoral prosthesis 10 would have to dig into or compress the tibial part 56 of the TKA prosthesis. However, the tibial prosthesis 56 is a relatively rigid body, and therefore, the only way the knee with a traditional prosthesis 10 can flex beyond 90 degrees is by stretching the soft tissue in the knee. This stretching of the soft tissue in a knee incorporating the traditional femoral prosthesis 10 is demonstrated in FIG. 8B by a change in position of the medial collateral ligament 58. Flexing of the knee with a traditional femoral prosthesis 10 becomes progressively more difficult with greater degrees of flexion. In fact, after about 110 degrees, the knee is typically too tight to flex any further. In contrast, the femoral prothesis 100 allows the knee to go into very deep flexion without having to overstretch the soft-tissue, thereby potentially enhancing the range of motion post-TKA surgery. Without overstretching the soft-tissue in the knee, the femoral prosthesis 100 also maintains more symmetric medial and lateral ligament balance through a full range of motion.

Figure 4B:
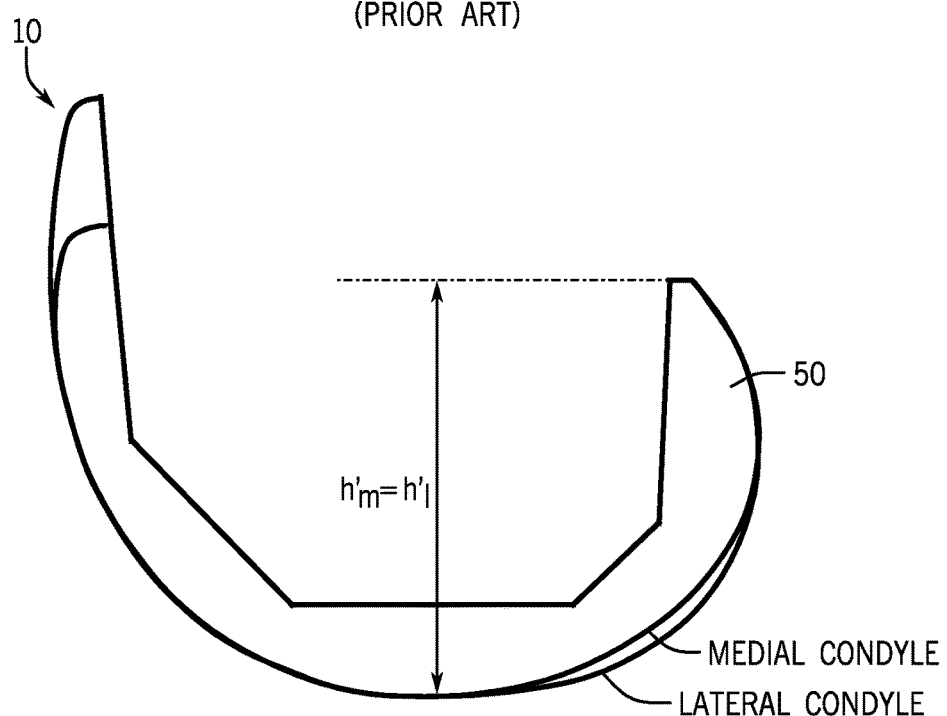
FIG. 4B provides a side view of a prior art TKA femoral prosthesis, displaying the profiles of the medial and lateral condyles. Herein the medial and lateral femoral condyles of the prior art prosthesis have equal heights ($h'_m = h'_l$).
Figure 4C:
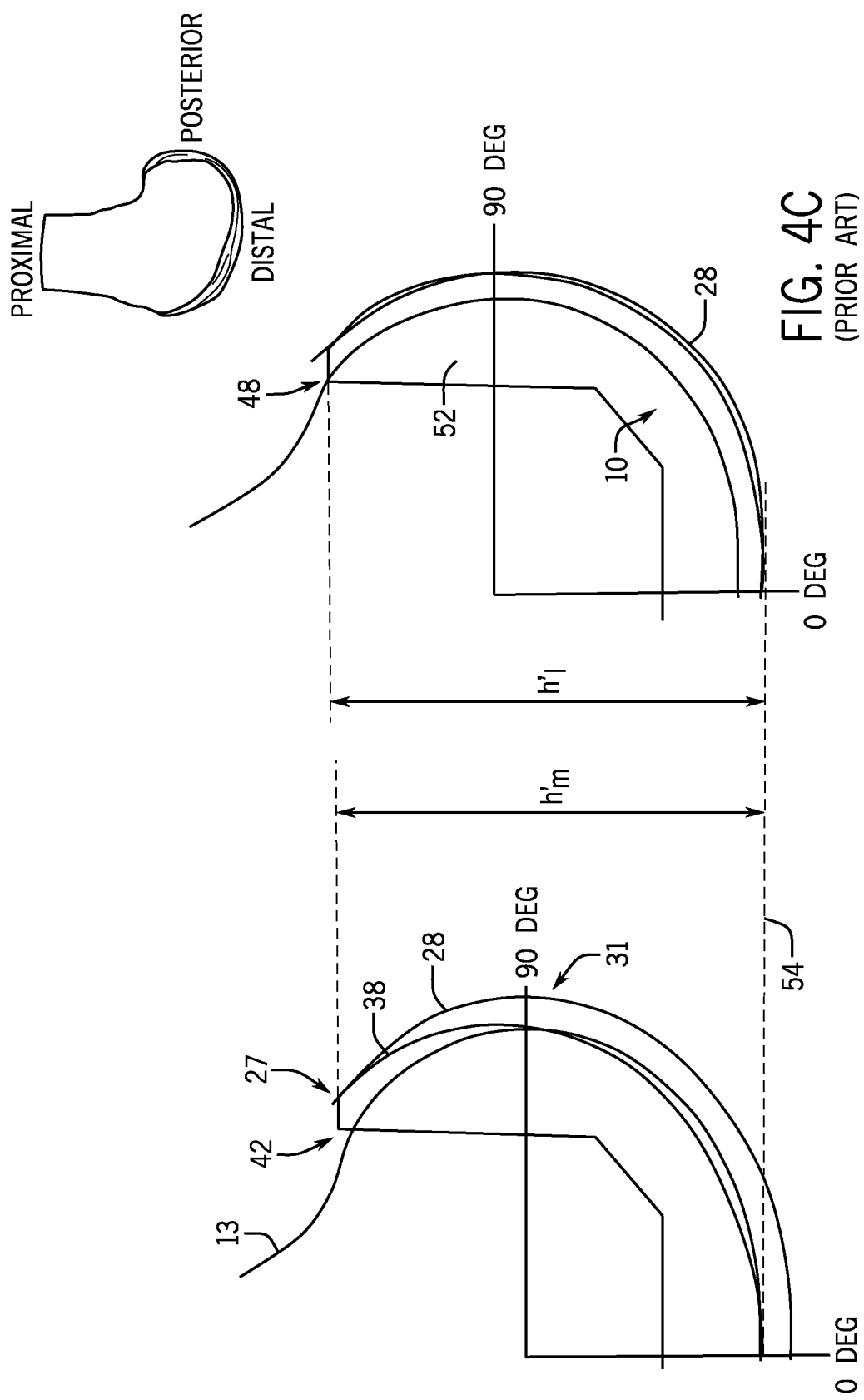
FIG. 4C provides sagittal sectional views of the prior art femoral prosthesis of FIG. 4A taken parallel to the femoral mechanical axis displaying both the medial and lateral condyles of the femoral prosthesis, in which the medial and lateral condyles of the femoral prosthesis have equal heights ($h'_m = h'_l$), and the medial side of the femoral prosthesis matches the level of the femoral bone in the distal and posterior regions, but is proud of the bone in the proximal-posterior region i.e. is shifted outwards relative to the femoral bone surface.
Figure 5A:
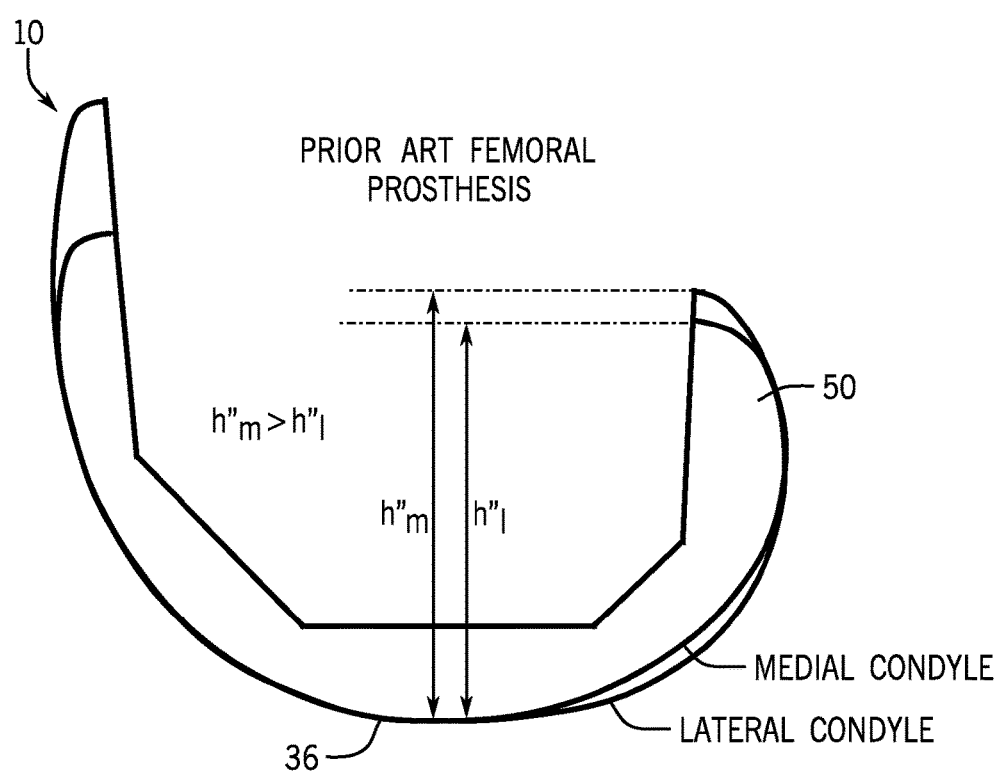
FIG. 5A shows a side view of another prior art femoral prosthesis, displaying the profiles of the medial and lateral condyles. Herein the height of the medial femoral condyle of the prior art femoral prosthesis is greater than the height of the lateral femoral condyle ($h''_m > h''_l$).
Figure 5B:
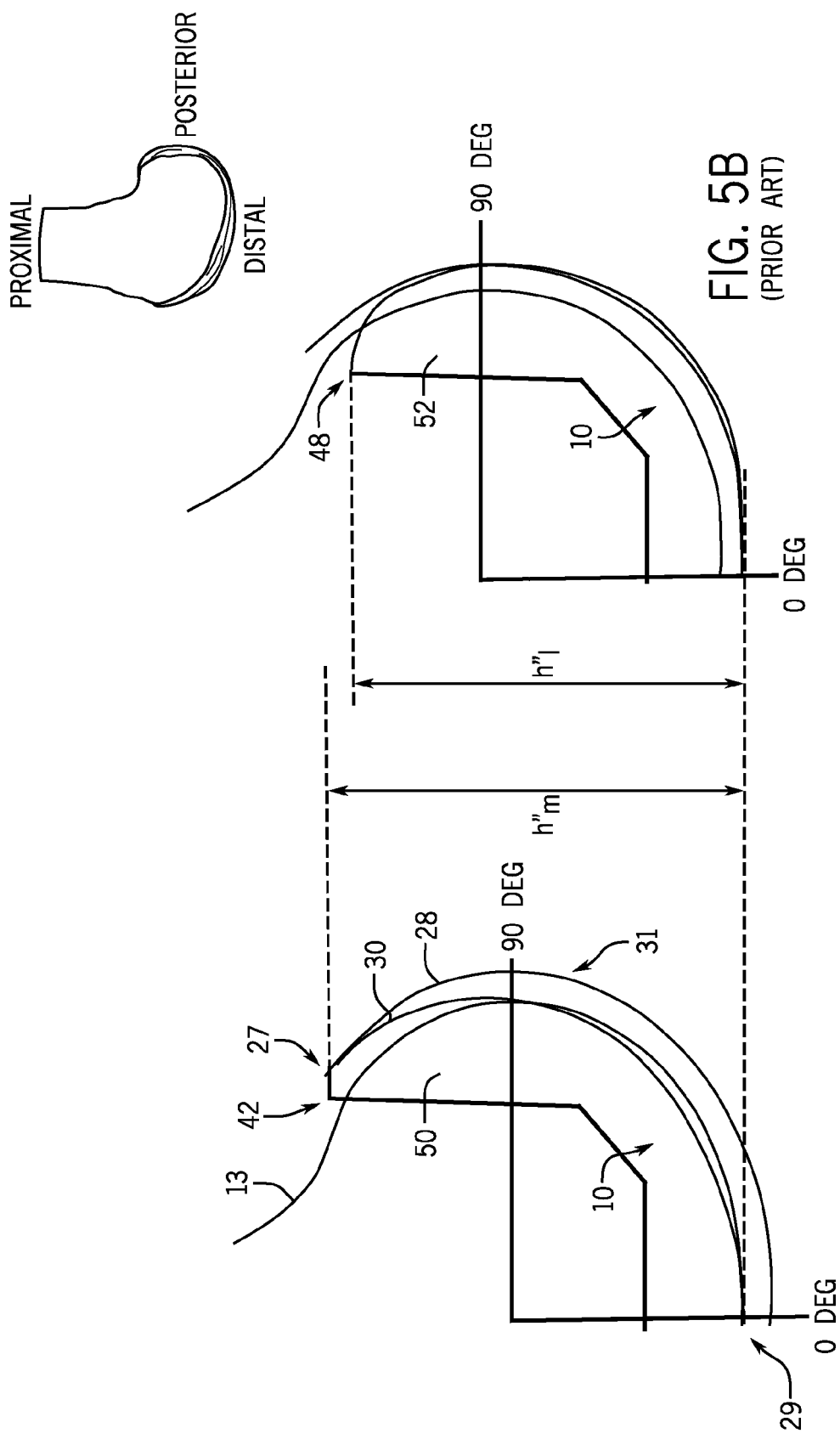
FIG. 5B shows sagittal sectional views of the prior art femoral prosthesis of FIG. 5A taken parallel to the femoral mechanical axis displaying both the medial and lateral condyles of the femoral prosthesis, in which the height of the medial condyle of the femoral prosthesis is greater than of the lateral condyle ($h''_m > h''_l$). Herein, the medial side of the femoral prosthesis matches the level of the femoral bone in the distal and posterior regions, but is proud of the bone in the proximal-posterior region i.e. is shifted outwards relative to the femoral bone surface.
Figure 9:
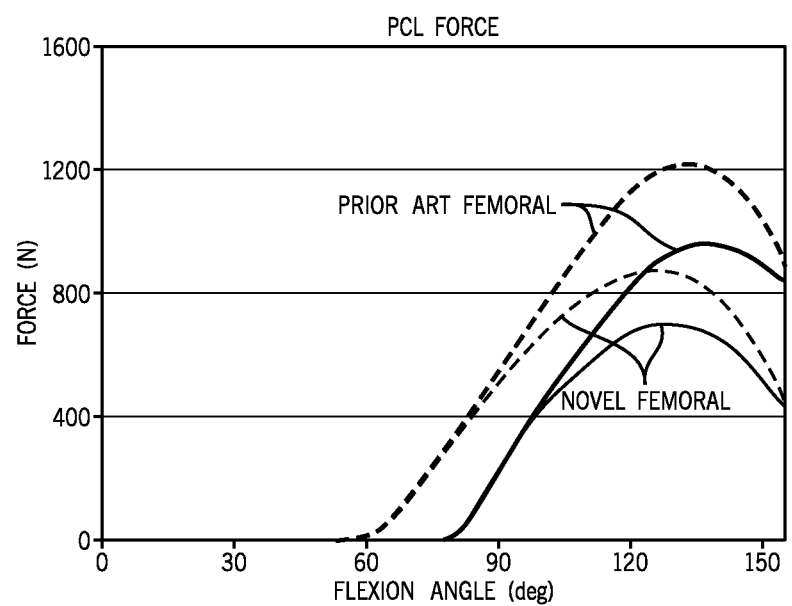
FIG. 9 provides a graph showing tension/force in the posterior cruciate ligament during a simulated deep knee bend activity with prior art femoral prosthesis of FIG. 4B and embodiment of the femoral prosthesis of FIG. 6A.

The performance of the femoral prosthesis of FIG. 6A was compared against prior art femoral prosthesis of FIG. 4B using a dynamic knee simulation software. Both femoral components articulated with identical tibial and patellar implants, and one full cycle of a deep knee bend (0 to 155 degrees flexion and 155 to 0 degree extension) was simulated. The kinematics of the knee, characterized as motion of medial and lateral femoral condyles relative to a fixed tibia, were virtually identical for both the traditional femoral prosthesis and that of the present disclosure. However, with the femoral prosthesis of the present disclosure the posterior cruciate ligament (PCL) tension was significantly reduced for knee flexion above 90 degrees compared to the traditional femoral prosthesis (reduction in tension of ~20 percent at 120 degrees flexion, FIG. 9). This validates the ability of the femoral prosthesis of the present invention to minimize soft tissue tightness in flexion, particularly for soft tissue on the medial side and/or soft tissue attaching to the medial femoral condyle.

The prosthesis described herein can be constructed in various manners and can be made from one or more materials. The prosthesis can be machined, cast, forged, molded, or otherwise constructed out of a medical grade, physiologically acceptable material such as a cobalt chromium alloy, a titanium alloy, stainless steel, ceramic, etc. Other, non-limiting examples of materials for the implants include polyolefins, polyethylene, ultra-high molecular weight polyethylene, medium-density polyethylene, high-density polyethylene, medium-density polyethylene, highly cross-linked ultra-high molecular weight polyethylene (UHMWPE), and the like.

The present invention provides an improved knee replacement prosthesis, which can facilitate deep knee flexion without creating excessive tension in the ligamentous structure of the knee. A knee replacement prosthesis, such as a TKA prosthesis, is generally composed of a femoral prosthesis that replaces at least a portion of the native femur, a tibial prosthesis that replaces at least a portion of the native tibia, and an optional patellar prosthesis that replaces at least a portion of the native patella. The present invention describes novel embodiments of femoral prosthesis for knee replacement. A TKA prosthesis is a tri-compartmental prosthesis designed to replace all three compartments of the knee, namely: the lateral compartment, medial compartment and the patellofemoral compartment. While, the femoral prosthesis of the present invention is described in relation to a tri-compartmental TKA prosthesis, these novel designs are applicable to knee replacement prosthesis involving replacement of one or more compartments of the knee (such as uni-compartment or bi-compartment), including implants with or without a tibial or patellar prosthesis.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A femoral prosthesis comprising:
    an internal non-articulating bone-engaging surface configured to be connected to a resected distal end of a femur;
    an external articulating surface including a distal articulating surface, a medial posterior surface having a first medial end and a second medial end, and a lateral posterior surface having a first lateral end and a second lateral end, wherein the first medial end and the first lateral end are connected to the distal articulating surface;
    a medial condyle extending from the first medial end to the second medial end and formed between the medial posterior surface and the internal non-articulating surface; and
    a lateral condyle extending from the first lateral end to the second lateral end and formed between the lateral posterior surface and the internal non-articulating surface;
    wherein a first height of the medial condyle measured from a line tangent to the distal articulating surface to the second medial end is less than a second height of the lateral condyle measured from the line tangent to the distal articulating surface to the second lateral end,
    wherein the medial posterior surface transitions from a posterior portion in which the medial posterior surface is not shifted inwards relative to the lateral posterior surface to a proximal-posterior portion in which the medial posterior surface is shifted inwards relative to the lateral posterior surface, when viewed in a lateral view such that an internal non-articulating bone-engaging surface of each of the medial and lateral condyles lie on a plane perpendicular to the lateral view, wherein a medial condyle posterior thickness measured in the lateral view from the internal non-articulating bone-engaging surface to a most posterior surface of the medial condyle is equal to a lateral condyle posterior thickness measured in the lateral view from the internal non-articulating bone-engaging surface to a most posterior surface of the lateral condyle, and wherein a medial condyle distal thickness measured in the lateral view from the internal non-articulating bone-engaging surface to a most distal surface of the medial condyle is equal to a lateral condyle distal thickness measured in the lateral view from the internal non-articulating bone-engaging surface to a most distal surface of the lateral condyle, and wherein a radius of the medial condyle is less than a radius of the lateral condyle, the radius of the medial condyle and the radius of the lateral condyle being measured between the most posterior surface and the second medial end.

2. The femoral prosthesis of claim 1, wherein the medial condyle further includes a proximal-posterior tip or end, the proximal-posterior tip or end having a smooth rounded profile.

3. The femoral prosthesis of claim 1, wherein a difference in height between the medial condyle and the lateral condyle is within the range of about 2 millimeters to about 5 millimeters.

4. The femoral prosthesis of claim 1, wherein the medial posterior surface transitions from a posterior portion in which the medial posterior surface is not shifted inwards relative to the lateral posterior surface to a distal-posterior portion in which the medial posterior surface is shifted inwards relative to the lateral posterior surface.

5. A femoral prosthesis comprising:
an internal non-articulating bone-engaging surface configured to be connected to a resected distal end of a femur;
an external articulating surface including a distal articulating surface, a medial posterior surface having a first medial end and a second medial end, and a lateral posterior surface having a first lateral end and a second lateral end, wherein the first medial end and the first lateral end are connected to the distal articulating surface;
a medial condyle extending from the first medial end to the second medial end and formed between the medial posterior surface and the internal non-articulating surface; and
a lateral condyle extending from the first lateral end to the second lateral end and formed between the lateral posterior surface and the internal non-articulating surface;

wherein a first height of the medial condyle measured from a line tangent to the distal articulating surface to the second medial end is less than a second height of the lateral condyle measured from the line tangent to the distal articulating surface to the second lateral end, wherein the medial posterior surface transitions from a posterior portion in which the medial posterior surface is not shifted inwards relative to the lateral posterior surface to a proximal-posterior portion in which the medial posterior surface is shifted inwards relative to the lateral posterior surface, wherein a medial condyle posterior thickness measured in a lateral view from the internal non-articulating bone-engaging surface to a most posterior surface of the medial condyle is equal to a lateral condyle posterior thickness measured in the lateral view from the internal non-articulating bone-engaging surface to a most posterior surface of the lateral condyle, and wherein a medial condyle distal thickness measured in the lateral view from the internal non-articulating bone-engaging surface to a most distal surface of the medial condyle is equal to a lateral condyle distal thickness measured in the lateral view from the internal non-articulating bone-engaging surface to a most distal surface of the lateral condyle, and wherein a radius of the medial condyle is less than a radius of the lateral condyle, the radius of the medial condyle and the radius of the lateral condyle being measured between the most posterior surface and the second medial end.

6. The femoral prosthesis of claim 5, wherein the medial condyle further includes a proximal-posterior tip or end, the proximal-posterior tip or end having a smooth rounded profile.

7. The femoral prosthesis of claim 5, wherein a difference in height between the medial condyle and the lateral condyle is within the range of about 2 millimeters to about 5 millimeters.

8. The femoral prosthesis of claim 5, wherein the medial posterior surface transitions from a posterior portion in which the medial posterior surface is not shifted inwards relative to the lateral posterior surface to a distal-posterior portion in which the medial posterior surface is shifted inwards relative to the lateral posterior surface.

* * * * *